United States Patent [19]

Goyert

[11] Patent Number: 5,804,189
[45] Date of Patent: Sep. 8, 1998

[54] TREATMENT OF LIPOPOLYSACCHARIDE- OR CD14-MEDIATED CONDITIONS USING SOLUBLE CD14

[75] Inventor: Sanna M. Goyert, 10 Waterside Plz., Apt. 36F, New York, N.Y. 10010

[73] Assignee: Sanna M. Goyert, New York, N.Y.

[21] Appl. No.: 254,095

[22] Filed: Jun. 6, 1994

Related U.S. Application Data

[63] Continuation-in-part of Ser. No. 863,913, Apr. 6, 1992, abandoned.
[51] Int. Cl.$^6$ ..................................................... A61K 38/17
[52] U.S. Cl. .......................... 424/185.1; 514/12; 530/350
[58] Field of Search ............................... 514/12; 530/350, 530/388.22, 388.23; 435/69.1; 536/23.5; 424/184.1, 185.1

[56] References Cited

FOREIGN PATENT DOCUMENTS

| 40 29227 A1 | 9/1990 | Germany . |
|---|---|---|
| PCT WO 91/01639 | 7/1990 | WIPO . |
| PCT WO 92/04908 | 9/1991 | WIPO . |

OTHER PUBLICATIONS

Malizevski, Wright, CD14 and Immune Response to Lipopolysaccharide, *Science*, 252:1321–1322(1991).
Goyert et al., The CD14 Monocyte Differentiation Antigen Maps to a Region Encoding Growth Factors and Receptors, *Science* 239:497–500 (1988).
Ferrero et al., Nucleotide sequence of the gene encoding the monocyte differentiation antigen, CD14, *Nuc. Acids Res.*, 16:4173(1986).
Matsuura et al., Nucleotide and amino acid sequences of the mouse CD14 gene, *Nucleic Acids Research*, 17:2132 (1989).
Setoguchi et al., Mouse and human CD14 (myeloid cell-specific leucine–rich glycoprotein) primary structure deduced from cDNA clones, *Biochim. Biophys. Acta*, 1008:213–222 (1989).
Bazil et al., Biochemical characterization of a soluble form of the 53–kDa monocyte surface antigen, *Eur. J. Immunol.*, 16:1583–1589 (1986).

Lauener et al., Interleukin 4 down–regulates the expression of CD14 in normal human monocytes, *Eur. J. Immunol.* 20:2375–2381 (1990).
Lauener et al., Engagement of the Monocyte Surface Antigen CD14 Induces Lymphocytes Function Associated Antigen–1/Intercellular Adhesion Molecule Dependant Homotypic Adhesion, *J. Immunol.*, 145:1390–1394 (1990).
Lund–Johansen et al., Signal transduction in human monocytes and granulocytes through the PI–linked antigen CD14, *FEBS Letters*, 273:1–2–55–88(1990).
Ulevitch et al., A New Model of Macrophage Stimulation by Bacterial Lipopolysaccharide, *The Journal of Trauma*, 30:189–192 (1990).
Ziegler et al., Treatment of Gram–Negative Bacteremia and Septic Shock with HA–1A Human Monoclonal Antibody Against Endotoxin, *The New England Journal of Medicine*, 324:429–436 (1991).
Haziot et al., Recombinant Soluble CD14 Inhibits LPS–Induced Tumor Necrosis Factor Necrosis Factor–α Production by Cells in Whole Blood, *Journal of Immunology*, 152:5868–5876 (1994). Jun. 15, 1994.
Scheirle et al., Peptide Binding to Soluble HLA–DR4 Molecules Produced by Insect Cells, *Journal of Immunology*, 149:1994–1999(1992).
Fraser, The Baculovirus–Infected Insect Cell as a Eukaryotic Gene Expression System, *Curr. Topics Microbiol. Immunol.*, 158:148–172 (1992).
M. Arditi et al., Infect. Immun. 61(8):3149–3156, 1993.
C. Schutt et al., Res. Immunol. 143(1):71–78, Jan. 1992.

*Primary Examiner*—Lorraine M. Spector
*Attorney, Agent, or Firm*—Iver P. Cooper

[57] ABSTRACT

Methods are provided for the treatment of symptoms of sepsis and other conditions that are mediated by the action of CD14 myelomonocytic antigen ("CD14"). The embodiments herein include treatments for symptoms of sepsis that are triggered by lipopolysaccharide ("LPS"). A genetically engineered recombinant soluble CD14 ("rsCD14") and fragments thereof are also provided. Both rsCD14 and a fragment thereof have been isolated and purified. The rsCD14 or fragments thereof can be administered to mammals to prevent or treat symptoms that are associated with sepsis.

12 Claims, 7 Drawing Sheets

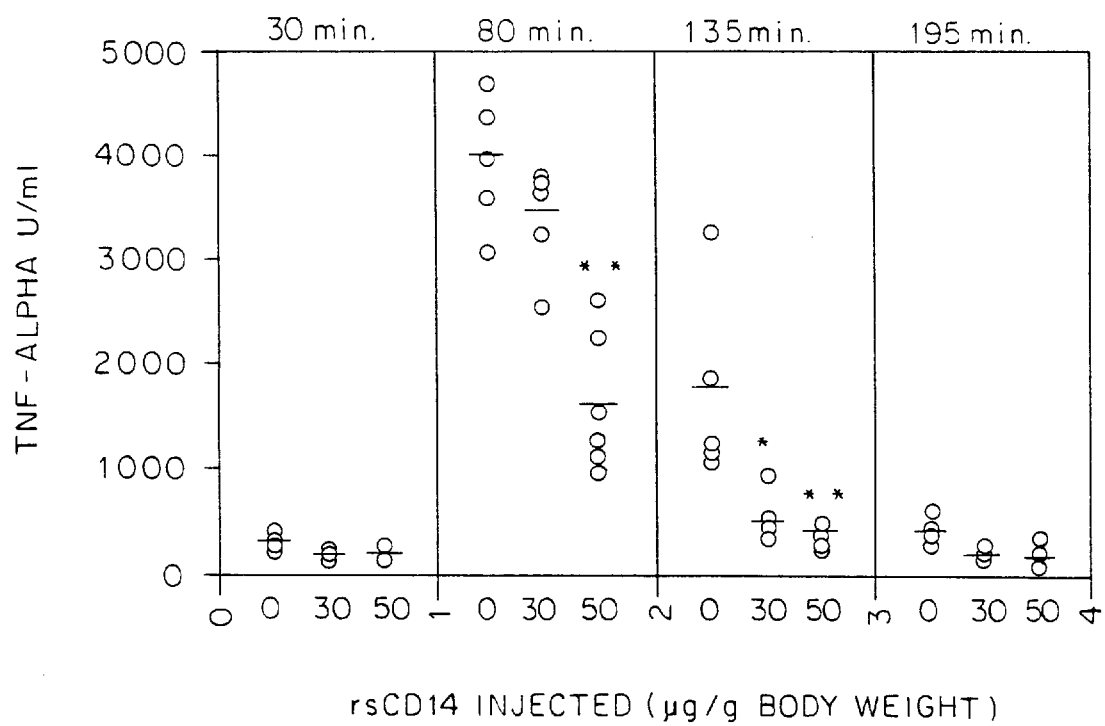

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Homo sapiens ( x i ) SEQUENCE DESCRIPTION: SEQ ID NO:1:

```
Ala  Glu  Leu  Gln  Gln  Trp  Leu  Lys  Pro  Gly  Leu  Lys  Val  Leu  Ser  Ile
 1                  5                        10                           15

Ala  Gln  Ala  His  Ser  Leu  Asn  Phe  Ser  Cys
              20                      25
```

TREATMENT OF LIPOPOLYSACCHARIDE- OR CD14-MEDIATED CONDITIONS USING SOLUBLE CD14

This application is a continuation-in-part of application Ser. No. 07/863,913 filed Apr. 6, 1992, now abandoned, which is hereby incorporated by reference.

FIELD OF THE INVENTION

This invention relates generally to methods and therapies for effectively preventing or treating the symptoms of diseased states such as sepsis, and for regulating the cellular and molecular mechanisms that result in sepsis. It also relates to the use of recombinant techniques to generate biomolecules that can be used in such treatments.

BACKGROUND OF THE INVENTION

Sepsis is a life-threatening medical condition that can be brought on by infection or trauma. R. Ulevitch, et al., *J. Trauma* 30: S189–92 (1990). The symptoms of sepsis can include chills, profuse sweating, fever, weakness, or hypotension, followed by leukopenia, intravascular coagulation, shock, adult respiratory distress syndrome, multiple organ failure, and often, death. R. Ulevitch, et al., *J. Trauma* 30: S189–92 (1990).

The symptoms associated with sepsis can be induced in animals by certain substances (elements, molecules, chemical compounds, or any mixture thereof) that are liberated during infection or trauma. Pathogenic bacteria, viruses, and plants elaborate sepsis-inducing substances.

Lipopolysaccharide ("LPS", also called endotoxin), a component of the outer membrane of Gram-negative bacteria, is the major mediator in the development of endotoxin-induced shock. While the precise chemical structures of LPS molecules obtained from different bacteria may vary in a species-specific fashion, a region called the lipid A region is common to all LPS molecules. E. Rietschel et al., in HANDBOOK OF ENDOTOXINS, 1: 187–214, eds. R. Proctor and E. Rietschel, Elsevier, Amsterdam (1984). This lipid A region mediates many, if not all, of the LPS-dependent pathophysiologic changes that characterize sepsis.

LPS is a primary cause of death in humans afflicted with gram-negative sepsis. van Deventer et al., *Lancet,* 1: 605 (1988); Ziegler et al., *J. Infect. Dis.,* 136: 19–28 (1987). Treatment of patients suffering from sepsis and gram-negative bacteremia with a monoclonal antibody against LPS decreased their mortality rate. Ziegler et al., *N. Eng. J. Med.,* 324: 429 (1991). LPS and gram-negative bacteria may also play a role in the pathology of autoimmune conditions such as Reiter's syndrome, which is associated with rheumatoid arthritis.

LPS causes polymorphonuclear leukocytes, endothelial cells, and cells of the monocyte/macrophage lineage to rapidly elaborate and release a variety of cell products, among these immunoregulatory substances that are capable of initiating, modulating or mediating humoral and cellular immune responses and processes. In vitro studies have shown that LPS induces monocytes/macrophage to release inflammatory cytokines such as TNFα, IL-1, and IL-6 which play a major role in the cascade of events leading to endotoxic shock.

One particular cytokine, tumor necrosis factor (TNF) or alpha-cachectin, is apparently a primary mediator of septic shock. Beutler et al., *N. Eng. J. Med.,* 316: 379 (1987). Intravenous injection of LPS into experimental animals and man produces a rapid, transient release of TNF. Beutler et al., *J. Immunol.,* 135: 3972 (1985); Mathison et al., *J. Clin. Invest.* 81: 1925 (1988). Pretreatment of animals with anti-TNF antibodies reduces lethality, suggesting that TNF is a critical mediator of septic shock. Beutler et al., *Science,* 229: 869, (1985); Mathison et al ., *J. Clin. Invest.* 81: 1925 (1988).

Molecular receptors that can combine with sepsis-inducing substances and initiate certain chemical reactions play a critical role in the etiology of the symptoms of sepsis. Several monocyte/macrophage surface antigens that possess receptor and signal transduction functions have been identified. Many of them are cell differentiation markers (i.e., they are characteristically present only in defined stages, especially the end stages, of cells of a defined lineage and function).

One such marker, CD14, is a 55-kD glycoprotein expressed strongly on the surface of monocytes and macrophages, and weakly on the surface of granulocytes such as neutrophils. S. M. Goyert et al., *J. Immunol.* 137: 3909 (1986); A. Haziot et al., *J. Immunol.* 141: 547–552 (1988); S. M. Goyert et al., *Science* 239: 497 (1988). CD14 is linked by a cleavable phosphoinositol tail [A. Haziot et al., *J. Immunol.* 141: 547–552 (1988)] to the exoplasmic surface of mature monocytes, macrophages, granulocytes and dendritic reticulum cells, of renal nonglomerular endothelium, and of hepatocytes in rejected livers. A soluble form of CD14 is present in minute concentrations in normal sera and in the urine of nephrotic patients. Bazil et al., *Eur. J. Immunol.* 16: 1583 (1986).

In vitro analyses have shown that CD14 is the receptor for lipopolysaccharide (LPS or endotoxin) when LPS is bound to an acute phase serum protein called LBP (LPS binding protein). LBP recognizes the lipid A region of LPS and forms high affinity 1:1 stoichiometric complexes. Tobias et al., *J. Biol. Chem.,* 264:10867 (1989). The binding of this complex to CD14 causes cells to become highly activated and release interleukins, tumor necrosis factor ("TNF"), $H_2O_2$, and other substances which eventually cause the lethal symptoms observed during sepsis, including the "shut-down" of the cardiovascular-pulmonary-renal systems. Beutler et al., *N. Eng. J. Med.,* 316:379 (1987); R. Ulevitch et al., *J. Trauma* 30:189–92 (1990); F. Lund-Johansen et al., *FEBS Lett.* 273: 55 (1990).

The cDNAs and the genes for human and murine CD14 have been cloned and sequenced. E. Ferrero and S. M. Goyert, *Nuc. Acids Res.* 16: 4173 (1988); S. M. Goyert et al., *Science* 239: 497 (1988); M. Setoguchi et al., N. Nasu, S. Yoshida, Y. Higuchi, S. Akizuki, and S. Yamamoto, *Biochem. Biophys. Acta* 1008: 213–22 (1989). The sequence analysis revealed that CD14 belongs to a family of leucine-rich membrane-bound and soluble proteins that have receptor and cell adhesive functions. M. Setoguchi et al., *Biochem. Biophys. Acta* 1008: 213–22 (1989); E. Ferrero, C. L. Hsieh, U. Francke and S. M. Goyert, *J. Immunol.* 145: 133 (1990).

The human CD14 protein sequence contains five potential sites for N-linked glycosylation and contains a 10 fold repeat of a leucine rich motiff (LXXLXLX). There is a 66% amino acid sequence identity between the murine and human CD14s. The murine gene is located on mouse chromosome 18, which like the human gene also contains at least five genes encoding receptors. M. Setoguchhi, N. Nasu, S. Yoshida, Y. Higuchi, S. Akizuki, and S. Yamamoto, *Biochem. Biophys. Acta* 1008: 213–22 (1989); E. Ferrero, C. L. Hsieh, U. Francke and S. M. Goyert, *J. Immunol.* 145: 133 (1990).

In situ chromosomal hybridization of the $^3$H-labelled cDNA probe to normal human metaphase cells resulted in specific labeling only of chromosome 5. S. M. Goyert et al., *Science* 239: 497 (1988). The labeled sites were clustered at regions 5q22–q32 of this chromosome. The largest cluster of grains was located at 5q23–q31. S. M. Goyert et al., *Science* 239: 497 (1988). This region of human chromosome 5 is known to contain a cluster of genes that encode several myeloid-specific growth factors or growth factor receptors, as well as other growth factor and receptor genes. S. M. Goyert et al., *Science* 239: 497 (1988). The mapping of the CD14 gene to this region of chromosome 5, its expression preferentially by mature myeloid cells, and its deletion in the malignant cells of patients having myeloid leukemias and del(5q) suggest that the CD14 antigen may play a role in the pathogenesis of myeloid disorders.

For the preceding reasons, it is an object of this invention to develop methods and therapies for the effective treatment, including prevention, for symptoms of sepsis in those individuals afflicted by symptoms of sepsis. It is also an object of this invention to develop methods and therapies for the effective protection of individuals who are at risk of becoming afflicted by the symptoms of sepsis.

It is a further object of the invention to provide methods and means for studying the mechanisms of ailments such as sepsis, as a model for diseases caused by host immune response to exogenous and endogenous triggers of the immune system. Such methods and means expressly include methods for the testing of substances that cause, mediate or prevent symptoms of sepsis. ("Cause" includes beginning molecular events that result in the symptoms of sepsis or are implicated in the organism's response to sepsis; "mediate" includes any molecular events that form part of the causal chain of events that result in the symptoms of sepsis or are part of the organism's response to sepsis.)

Finally, it is an object of this invention to develop methods and therapies for the effective treatment, including prevention, of symptoms of tissue rejection and of autoimmune disease that are mediated by LPS, gram-negative bacteraemia, and/or CD14.

SUMMARY OF THE INVENTION

A new therapy has been developed for treatment of symptoms of sepsis and other conditions that are mediated by the CD14 receptor. A soluble form of the recombinant human CD14 ("rsCD14") receptor was produced by using molecular genetic techniques to express an isolated nucleic acid sequence that encodes human CD14 in a Baculovirus expression system. The soluble form of the human CD14 was isolated and purified. When injected into mice exposed to endotoxin (also, "LPS"), the rsCD14 protected the mice against the lethal effects of endotoxin.

BRIEF DESCRIPTION OF DRAWINGS

FIG. 1A: Saturable binding of bovine lipopolysaccharide (b LPS) to immobilized rsCD14 in the presence of LBP. Plates were coated with recombinant soluble rsCD14, naturally occurring soluble nsCD14, or murine IgG at 16 μg/ml. Increasing concentrations of bLPS were preincubated with purified LBP (40 μg/ml) and added to the plate. Specific binding was calculated by subtraction of the amount of bLPS bound to wells coated with PBS-gelatin (0.5%). Closed square, rsCD14 coated wells; closed triangle, nsCD14 coated wells; open circle, IgG coated wells. The results are representative of two assays. FIG. 1B: Effect of LBP on the binding of bLPS to immobilized rsCD14. Plates were coated with rsCD14 at 32 μg/ml. Increasing concentrations of bLPS were preincubated with or without purified LBP or with BSA and added to the plate. Specific binding was calculated by subtraction of the amount of bLPS bound to wells coated with PBS-gelatin (0.5%). Closed square, LBP 1.4 μg/ml; open triangle, LBP 0.7 μg/ml; closed circle, no LBP; open circle, BSA 0.7 μg/ml. The results are representative of two assays.

FIG. 6. In vivo inhibition of LPS-induced TNFα secretion by rsCD14. Eight week old mice were weighed and injected i.p. with an $LD_{50}$ of LPS (*Salmonella Minnesota*, wild type, 13 μg/gbw) in 0.1 ml saline immediately followed by a second i.p. injection of saline or rsCD14 (30 or 50 μg/gbw). At 30, 80 and 135 minutes following the injections, the mice were bled from the tail vein (30 μl) and the serum concentration of TNFα was measured by a bioassay using WEHI-2F cells and the MTT cytotoxicity assay (A. Haziot, B. Tsuberi, S. M. Goyert, *J. Immunol.* 150, 5556 (1993)). TNFα concentrations were calculated by Probit analysis.

FIG. 7A: PBMC: cells ($8 \times 10^5$) were incubated in the presences of LPS (0.5 ng/ml) and increasing concentrations of rsCD14 or globulin-free BSA in 1% autologous plasma for 3 h. TNF-α was measured in cell-free supernatants by ELISA. In the absence of inhibitor, the TNF-α concentration was 1.24 ng/ml. Closed square, rsCD14; open circle, globulin-free BSA. The results are representative of five assays. 7B: Macrophage cell lines: cells ($8 \times 10^4$) were incubated in the presences of LPS (0.25 ng/ml) and increasing concentrations of rsCD14 in SFM. After 3 h incubation, TNF-α was measured in cell-free supernatants by bioassay using WEH1-2F cells and the MTT cytotoxicity assay. TNF-α concentrations were calculated by Probit analysis. In the absence of inhibitor, the TNF-α concentration was 16.4 U/ml. The results are representative of two assays. 7C: Whole blood: increasing concentrations of rsCD14 or globulin-free BSA were added to whole blood immediately before adding LPS at 0.25 ng/ml (squares and circles) or 0.1 ng/ml (triangles). After incubation at 37° C. for 3 h, the cells were pelleted and the supernatants assayed for TNF-α by ELISA. In the absence of inhibitor, the TNF-α concentrations were 1.72 [LPS 0.25 ng/ml] and 0.65 ng/ml (LPS 0.1 ng/ml). Closed triangle, rsCD14 added (LPS 0.1 ng/ml); open square, rsCD14 added (LPS 0.25 ng/ml); open circle, globulin-free BSA added (LPS 0.25 ng/ml). The results are representative of five assays.

DETAILED DESCRIPTION OF THE INVENTION

Figure 1A:
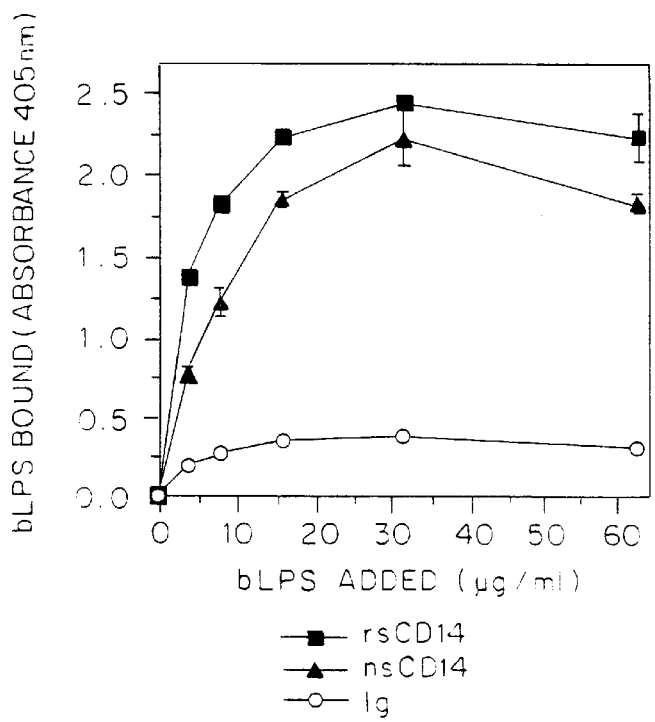
FIGS. 1A–1B.

When the subject matter of the instant invention was filed in the form of its parent application, there was considerable uncertainty about whether administration of soluble CD14 would be effective to treat symptoms of sepsis, given that serum concentrations of endogenous soluble CD14 were calculated to be a thousand (!) times greater than the peak concentration of LPS observed in human serum during sepsis. S. D. Wright, *Science* 252: 1321–1322 (1991) (Response to Letter, Technical Comments Section). Indeed, because murine endothelial cells have been shown to be activated by LPS in the presence of serum (E. E. Sikorski, R. Hallmann, E. L. Berg, E. C. Butcher, *J. Immunol.* 151, 523 (1993); M. Sironi et al., *Eur. J. Immunol.* 23, 2692 (1993)), it might be expected that the injection of mice with LPS and high doses of rsCD14 would lead to death.

However, the results presented below indicate that mice injected with LPS and rsCD14 recovered quickly after an initial period of shock-like symptoms. Thus, the fact that in practice the administration of soluble CD14 or of a fragment thereof protects against death is unexpected in view of the gross excess of endogenous sCD14 over expected calculated LPS levels during sepsis, and surprising in view of the demonstrated agonist effects of soluble CD14 on the endothelial response to LPS.

A Definitions.

It is important to an understanding of the present invention to note that all technical and scientific terms used herein, unless otherwise defined, are intended to have the same meaning as commonly understood by one of ordinary skill in the art; that techniques employed herein are also those that are known to one of ordinary skill in the art, unless stated otherwise; and that publications mentioned herein are incorporated by reference. It is also important to a clear understanding of the present invention that a number of the terms used herein are not intended to be limiting, even though common usage might suggest otherwise.

It is also important to note that the present invention is not limited to the use of all of the described discoveries or embodiments explicitly described herein. Although combining them may indeed be preferred, it is not necessary to the invention that all aspects be used simultaneously.

The term "nucleic acid" is used interchangeably with gene, cDNAs, RNA, or other oligonucleotides that encode gene products.

"Vector" denotes a genetically engineered nucleic acid construct capable of being modified by genetic recombinant techniques to incorporate any desired foreign nucleic acid sequence. A vector may be used as a means to introduce said sequence in a host cell, replicate it, clone it, and/or express said nucleic acid sequence, wherein said vector comprises all the necessary sequence information to enable the vector to be replicated in host cells, and/or to enable the nucleic acid sequence to be expressed, and/or to enable recombination to take place, and/or to enable the vector to be packaged in viral particles. This recitation of the properties of a vector is not meant to be exhaustive.

"Expression system" comprises all those combinations of host cells, vectors and growth conditions that are appropriate for expressing a nucleic acid, including inserting the nucleic acid into a vector and introducing the vector into a host cell capable of expressing the nucleic acid. An example is the Baculovirus system used herein.

"Modification" of a nucleic acid includes all molecular alterations of a nucleic acid sequence that change its capacity to perform a stated function, specifically including deletions, insertions, chemical modifications, and the like. Insertions and deletions may be made in a number of ways known to those skilled in the art, including enzymatically cutting the full length sequence followed by modification and ligation of defined fragments, or by site-directed mutagenesis, especially by loop-out mutagenesis of the kind described by Kramer et al. (1984), Nucl. Acids Res. 12: 9441–9456.

The terms "recombinant" and recombination do not refer to instances of genetic recombination that occur without the intervention of an experimenter; they rather denote instances of genetic recombination that are planned and facilitated by the use of genetic engineering techniques. Thus, recombinant CD14 refers to a molecule that is the contemplated result of the experimental manipulations described herein.

"Fragment" or "subfragment" refers to an isolated nucleic acid or polypeptide derived respectively from a larger nucleic acid sequence or a larger polypeptide sequence. Nucleic acid fragments may be generated by cutting, excising or deleting one or more nucleotides at any position of the reference sequence using known recombinant techniques, or by inserting a predetermined sequence of nucleotides at any predetermined position within the reference sequence using known recombinant techniques. Peptide fragments of proteins may be generated by direct proteolytic digestion of proteins, or by expressing genetically engineered nucleic acid fragments of a nucleic acid that encodes the full size protein.

"Expression of" or "expressing" a foreign nucleic acid, gene or cDNA is used hereinafter to encompass the replication of a nucleic acid, the transcription of DNA and/or the translation of RNA into protein, in cells or in cell-free systems such as wheat germ or rabbit reticulocytes. The term "foreign" indicates that the nucleic acid is not found in nature identically associated with the same vector or host cell, but rather that the precise association between the said nucleic acid and the vector or host cell is created by genetic engineering. It is not intended that the invention be limited to the use of nucleic acid sequences from any particular species or genus, but that this invention can be carried out using nucleic acids from a variety of sources. It is contemplated that any nucleic acid from any source may be inserted into the vector, with or without control elements.

Where the exogenous nucleic acid is to be expressed in a host which does not recognize the nucleic acid's naturally occurring transcriptional and translational regulatory regions, a variety of transcriptional regulatory regions may be inserted upstream or downstream from the coding region, some of which are externally inducible. Illustrative transcriptional regulatory regions or promoters for use in bacteria include the β-gal promoter, lambda left and right promoters, trp and lac promoters, trp-lac fusion promoter, and also the bacteriophage lambda $P_L$ promoter together with the bacteriophage lambda $O_L$ operator and the CI857 temperature-sensitive repressor, for example, to provide for temperature sensitive expression of a structural gene. Regulation of the promoter is achieved through interaction between the repressor and the operator. For use in yeast, illustrative transcriptional regulatory regions or promoters include glycolytic enzyme promoters, such as ADH-I and -II promoters, GPK promoter, and PGI promoter, TRP promoter, etc.; for use in mammalian cells, transcriptional control elements include SV40 early and late promoters, adenovirus major late promoters, etc. Other regulatory sequences useful in eucaryotic cells can include, for example, the cytomegalovirus enhancer sequence, which can be fused to a promoter sequence such as the SV40 promoter to form a chimeric promoter, or can be inserted elsewhere in the expression vehicle, preferably in close proximity to the promoter sequence.

When desired, expression of structural genes can be amplified by, for example, ligating in tandem a nucleic acid for a dominant amplifiable genetic marker 5' or 3' to the structural gene and growing the host cells under selective conditions. An example of an amplifiable nucleic acid is the gene for dihydrofolate reductase, expression of which may be increased in cells rendered resistant to methotrexate, a folate antagonist.

Recombinant DNA constructs prepared for the purposes of this invention may be introduced into the host in accordance with known techniques, such as transformation, transfection using calcium phosphate-precipitated DNA, electroporation, transfection with a recombinant virus, microinjection of the DNA into cells or the like.

The isolated nucleic acids of this invention can be used to generate modified polypeptides, each having at least one characteristic of the native polypeptide. These include subfragments, deletion mutants, processing mutants, or substitution mutants, polypeptides having the same secondary structure as the binding region of the native polypeptide, and combinations thereof. Such modified polypeptides may carry the functionality of the "wild type" peptide, or may have a modified or externally regulatable functionality. Such modified polypeptides may have considerable utility in the present invention, as would be appreciated by those skilled in the art.

"Wild type", mutant and analogous polypeptides and compositions thereof may be used for making antibodies, which may find use in analyzing results of the assays described as part of this invention. The antibodies may be prepared in conventional ways, either by using the subject polypeptide as an immunogen and injecting the polypeptide into a mammalian host, e.g., mouse, cow, goat, sheep, rabbit, etc., particularly with an adjuvant, e.g., complete Freund's adjuvant, aluminum hydroxide gel, or the like. The host may then be bled and the blood employed for isolation of polyclonal antibodies, or the peripheral blood lymphocytes (B-cells) may be fused with an appropriate myeloma cell to produce an immortalized cell line that secretes monoclonal antibodies specific for the subject compounds.

Vectors, optionally containing a foreign nucleic acid, may be "introduced" into a host cell, tissue or organism in accordance with known techniques, such as transformation, transfection using calcium phosphate-precipitated DNA, electroporation, gene guns, transfection with a recombinant virus or phagemid, infection with an infective viral particle, injection into tissues or microinjection of the DNA into cells or the like. Both prokaryotic and eukaryotic hosts may be employed, which may include bacteria, yeast, plants and animals, including human cells.

Once a given structural gene, cDNA or open reading frame has been introduced into the appropriate host, the host may be grown to express said structural gene, cDNA or open reading frame. Where the promoter is inducible, permissive conditions may be employed (for example, temperature change, exhaustion, or excess of a metabolic product or nutrient, or the like).

The expression vehicles used or provided herein may be included within a replication system for episomal maintenance in an appropriate cellular host, they may be provided without a replication system, or they may become integrated into the host genome.

It is important to recognize that the present invention is not limited to the use of such cells as are used herein. Cells from different species or different tissues (breast epithelium, colon, neuronal tissue, lymphocytes, etc.) may also be used.

"Symptom associated with sepsis" denotes one or several of the following: chills, profuse sweating, fever, weakness, hypotension, leukopenia, intravascular coagulation, shock, respiratory distress, organ failure, prostration, ruffled fur, diarrhea and eye exudate, and death, alone or in combination. This list is not meant to be exclusive, but may be supplemented with symptoms or combinations of symptoms that a person of ordinary skill would recognize are associated with sepsis. Such "symptoms associated with sepsis" that are treatable with CD14 they are within the scope of this invention. A symptom associated with sepsis may also be associated with another condition.

It is important to note that reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, etc., such that a different but known way is used to achieve the same goals as those to which the use of a suggested method, material or composition is directed.

The following examples and instructions are not intended in any way to be limiting, as it should be readily apparent to those skilled in the art how alternative means might be used to achieve the results that this invention provides.

The following experimental methods, having been used by us to demonstrate and illustrate the present invention, are described in substantial detail hereinbelow. However, these details are not intended to be limiting, and those skilled in the art will appreciate that many other methods could be used to verify and explore the screening methods and cell lines that comprise the present invention.

B. Isolation and characterization of the human CD14 gene.

A human cDNA library was constructed in pCD, the Okayama-Berg eukaryotic expression vector [H. Okayama and P. Berg, *Mol. Cell Biol.* 3: 280 (1983)] using messenger RNA (mRNA) isolated from human M4-AML (myelomonocytic) cells. S. M. Goyert et al., *Science* 239:497 (1988). 1.0 to 2.65 kb cDNA inserts were size-selected in low-melting agarose gels according to T. Yokota et al., *Proc. Natl Acad. Sci.* 81: 1070 (1984). S. M. Goyert et al., *Science* 233: 497 (1988). *Escherichia coli* (RR1) were then transformed with the cDNA and plated on agar. A total of 1056 colonies were randomly selected, transferred individually to small liquid cultures, and grown overnight at 37°

C. The 1056 liquid cultures were consolidated into 44 pools of 24 liquid cultures each. Each pool was grown in 500 ml of Luria broth containing 100 μg of ampicillin per milliliter, and plasmid DNA was isolated from each pool and used to transfect COS 7 cells as described by S. M. Goyert et al., *Science* 239: 497 (1988).

The COS 7 cells transfected with the 44 plasmid pools were analyzed for cell surface expression of CD14 by indirect immunofluorescence using a monoclonal antibody (MoS39) to CD14, [Dimitiu-Bona et al., *J. Immunol.* 130: 145 (1983)] and a fluoresceinated sheep antibody to mouse immunoglobulin. Five of the clones derived from these pools were positive for human CD14 expression. S. M. Goyert et al., *Science* 239: 497 (1988).

Each of the 24 plasmids from one of the positive pools was isolated on a cesium chloride gradient, transfected individually into COS 7 cells, and screened for CD14 expression as described above. One cDNA clone, labelled pCD-CD14, was found to express CD14. S. M. Goyert et al., *Science* 239: 497 (1988).

To confirm that the pCD-CD14 clone encoded authentic CD14 molecules, immunoprecipitates prepared from pCD-CD14-transfected COS 7 cells and from M4-AML cells expressing endogenous CD14 were compared by SDS-polyacrylamide gel electrophoresis. The molecules precipitated from both sources were nearly identical in size. S. M. Goyert et al., *J. Immunol.* 137: 3909 (1986). In addition, the pCD-CD14 probe was found to hybridize to a single mRNA species that showed an expression profile identical to CD14: it was present in monocytes, granulocytes and M4-AML cells, but not in less mature myeloid cells represented by the leukemic cell lines k62 (undifferentiated), U937 (monoblast-like), HL60 (promyelocyte-like), or M2-AML (myeloblastic with maturation) cells or lymphocytes. S. M. Goyert et al., *Science* 239: 497 (1988). The predicted protein sequence of the pCD-CD14 clone corresponded to the partial protein sequence of CD14 determined by microsequence analysis.

The pCD-CD14 cDNA clone was found to consist of 1367 nucleotides with a polyadenylate tail at the 3' end. S. M. Goyert et al., *Science* 239: 497 (1988). An initiation codon was identified at position 105, followed by an open reading frame (coding region) consisting of 1125 nucleotides flanked by 104 nucleotides of 5' untranslated sequence and 126 nucleotides of 3' untranslated sequence. Comparison with the partial protein sequence determined by microsequence analysis confirms the identity of this clone as encoding CD14 and indicates the presence of a signal peptide of 19 amino acids (−19 to −1).

The human CD14 gene was isolated from a size-selected (6 kb average) Eco RI genomic library constructed in the lambda vector gtWes. S. M. Goyert et al., *Science* 239: 497 (1988). DNA sequence analysis demonstrated that the human CD14 gene contains a single intron of 88 base pairs immediately after the ATG translational start site. E. Ferrero and S. M. Goyert, *Nuc. Acids Res.* 16: 4173 (1988). The initiation codon is flanked by a sequence which shows homology to the consensus sequence $C(C)^A{}_GCCATCC$ for a translation initiation site [as defined by M. Kozak, *Nucl. Acids Res.* 15: 8125–8148 (1987)] and is separated from the rest of the coding region by the 88 bp intron.

Southern blot analysis of DNA digested with several different restriction enzymes and probed with CD14 cDNA gave single bands, suggesting that CD14 is encoded by a single gene. S. M. Goyert et al., *Science* 239: 497 (1988).

C. Production, purification, and analysis of soluble recombinant CD14.

Recombinant CD14 was produced using the Baculovirus expression system. G. E. Smith et al., *Proc. Natl. Acad. Sci. USA*, 82: 8404 (1985); V. Luckow and M. Sommers, *Biotechnology* 6: 47 (1988). Briefly, a human CD14 (HCD14) recombinant transfer vector (pBlueBac-HCD14) was constructed by ligating a blunt-ended human CD14 cDNA Nco1-Mse1 fragment into a Nhe1 digested, blunt-ended pBlueBac transfer vector (Invitrogen Co, San Diego, Calif.) using routine procedures. Insect cells (*Spodoptera frugiperda* Sf9 cells, GIBCO/BRL, Gaithersburg, Md.) were grown in Sf-900 II serum free medium (SFM) (GIBCO/BRL) in T75 tissue culture flasks at 27° C. for monolayer cells or in Erlenmeyer flasks with shaking at 150 rpm, 27° C. for suspension cells. The Sf9 cells ($2.2 \times 10^6$ cells, viability >98%) were seeded in a T25 flask in Sf-900 II SFM to 50–60% confluency and incubated at 27° C. for one hour. After cell attachment, the Sf-900 II SFM was removed from the flask and replaced with 0.75 ml of fresh Sf-900 II SFM, and an equal volume of calcium phosphate transfection buffer (Invitrogen) containing 1 μg of wild-type *Autographa californica* nuclear polyhedrosis virus (AcMNPV) DNA (Invitrogen Co.) and 2 μg of the pBlueBac-HCD14 cDNA transfer vector was added in a dropwise manner. The cells were incubated at 27° C. for 4 h, washed twice with Sf-900 II SFM and cultured for 7 days at 27° C. in 4 ml of Sf-900 II SFM. The culture medium containing both wild-type and recombinant virus was harvested following centrifugation at 4000 rpm for 15 min and stored at 4° C. for further purification.

To isolate the HCD14 recombinant baculovirus, culture medium containing both wild-type and recombinant virus was diluted 1000-fold and used to infect Sf9 cells grown in 100 mm tissue culture dishes for 1 h at 27° C. The medium was then removed and 10 ml of 1.25% agarose (Invitrogen Corp.) containing Bluo-gal (150 μg/ml) (GIBCO-BRL) was added. Summers, M. D. and G. E. Smith, in A MANUAL OF METHODS FOR BACULOVIRUS VECTORS AND INSECT CELL CULTURE PROCEDURES, Texas Experimental Station Bulletin No. 1555, Texas A&M University, Colloegfe Station, Tex. (1988). When the agarose had solidified, the plates were incubated at 27° C. in a humidified atmosphere. After 7 to 10 days, wild-type and blue HCD14 recombinant viral plaques appeared. The blue plaques were picked up with a sterile pasteur pipet, amplified in Sf9 cells grown in wells of a 24-well tissue culture plate, and re-purified by this procedure for a total of 2 rounds. For the final round of isolation, the infected Sf9 cells were carefully checked under a microscope to eliminate the possibility of a mixture of recombinant and wild-type viral plaques. Recombinant viral stocks were prepared in Sf9 cells and grown in SF-900 II SFM at a multiplicity of infection (mol) of 0.1. After 6 days, the virus-containing culture medium was harvested by centrifugation at 5000 rpm for 30 min and stored at 4° C. The plaque forming unit (pfu) of the virus-containing supernatant was determined by plaque assay. Summers, M. D. and G. E. Smith, in A MANUAL OF METHODS FOR BACULOVIRUS VECTORS AND INSECT CELL CULTURE PROCEDURES, Texas Experimental Station Bulletin No. 1555, Texas A&M University, Colloegfe Station, Tex. (1988). The presence of the HCD14 cDNA and mRNA transcript in the infected Sf9 cells was confirmed by Southern and Northern blot analysis, respectively (data not shown).

The insect cells expressed human CD14 at the cell surface, as determined by cytofluorometry. (data not shown) Briefly, Sf9 cells ($6 \times 10^5$) were infected with recombinant virus and cultured as described above in serum-free media for 2 days. The cells were then washed with RPMI-1640 three times, resuspended in 0.5 ml of RPMI 1640 with either 0, 1 or 5 units/ml of PI-PLC (kindly provided by Dr. Martin Low, New York) and incubated at 37° C. for 1 h. The cells were then washed three times with PBS (pH 6.7) containing 5% newborn calf serum (NCS) (GIBCO/BRL) and stained for the expression of HCD14. For staining, the cell pellets were incubated on ice for 10 min with 50 μl of 10% casein (Sigma Chemical Co., St. Louis, Mo.) (prepared in PBS) to prevent non-specific binding. Cells were then divided in two and incubated on ice for 30 min with either 50 μl of phycoerythrin (PE) conjugated anti-human CD14 (IOM2, AMAC, Westbrook, Me.) or a murine PE-conjugated IgG2a isotype-matched control antibody. Cells were then washed 3 times in PBS containing 5% NCS and fluorescence was evaluated by quantitative cytofluorography on an EPICS-Profile II (Coulter Electronics, Hialeah, Fla.).

In addition to HCD14 expressed on the surface of the insect cells, a soluble form of HCD14 was also produced. Sf9 insect cells or BTI-TN-5B1-4 (High Five) cells derived from Trichoplusia ni egg cell homogenates (Invitrogen) were grown in SF-900 II serum free medium in 500 ml sterile Erlenmeyer flasks (27° C., shaking at 150 rpm) and infected with the recombinant HCD14 virus (moi=10). After 1 h, the cells were washed once with media and resuspended in SF-900 II SFM at a concentration of $1 \times 10^6$ cells/ml. The cells were incubated at 150 rpm, 27° C. for 3 days. Culture medium was then collected following centrifugation at 5,000 rpm for 60 minutes and filtered through a 0.22 micron filter.

Recombinant soluble human CD14 (rsCD14) was purified by affinity chromatography using an anti-CD14 antibody, S39, covalently bound to sepharose 4B (Pharmacia, Gaithersburg, Md.). Briefly, the culture supernatant was passed over the column and the column was sequentially washed with buffers containing 140 mM NaCl/10 mM Tris-HCl pH 8.0 followed by 500 mM NaCl/50 mM Tris-HCl pH 8.0, pH 9.0, pH 9.5 and pH 10.0 until the $OD_{280}$ of the effluent reached zero with each buffer. The column was eluted using 50 mM Glycine/150 mM NaCl, pH 2.5. The eluate was immediately neutralized in 1.0M Tris-HCl pH 9.0, dialyzed against four successive changes of phosphate-buffered saline (PBS) at 4° C. and sterile filtered.

rsCD14 is seen to be comprised of multiple bands and is smaller in size (45 kD) than native soluble CD14 (55 kD). The identity of the multiple bands was confirmed by Western blot. (FIG. 1)

In order to determine whether the molecular weight heterogeneity of the recombinant CD14 was due to differences in glycosylation, soluble CD14 was digested with a variety of glycosidases including native and recombinant forms of N-glycanase (PNGase, an enzyme which catalyzes the hydrolysis of Asn-linked oligosaccharides at the β-aspartylglucosylamine bond between the innermost GlcNAc and the asparagine residue, resulting in complete removal of the oligosaccharide) and Endoglycosidase H (an enzyme which catalyzes the hydrolysis of the glycosidic bond within the chitobiose core of high mannose and certain hybrid oligosaccharides and thus does to completely remove the oligosaccharide) and analyzed the products by SDS-PAGE. A single band with an apparent molecular weight of 35 kDa was obtained when rsCD14 was digested with native or recombinant N-glycanase (PNGase F) (data not shown). As expected, digestion with Endoglycosidase H did not completely remove all of the heterogeneity and resulted in two bands with apparent molecular weights of 42 kDa and 38 kDa. These studies indicate that the observed molecular weight heterogeneity of rsCD14 is due to glycosylation differences.

Soluble HCD14 expressed by mammalian cells lacks a GPl anchor. A. Haziot et al., *J. Immunol.* 141: 547–552 (1988). In order to determine whether the soluble form of HCD14 produced by the insect cells also lacks the GPl anchor, High Five cells were infected with recombinant virus and labelled in culture with $^3$H-proline (to label the protein portion of HCD14) or $^3$H-ethanolamine (to label the GPl anchor). SDS-PAGE analysis of labelled recombinant HCD14 isolated from the labelled cell lysates and culture media show that while $^3$H-labelled HCD14 was obtained from both the cell lysate and culture medium of $^3$H-proline labelled cells, only the membrane bound form could be isolated from $^3$H-ethanolamine labelled cells, indicating that the soluble form of recombinant HCD14 produced by the insect cells lacks the GPl anchor. (data not shown).

For the functional studies described below, the affinity-purified material was subsequently treated with protein A to remove any contaminating monoclonal antibody which might have eluted from the affinity column. Contaminating LPS was removed with polymyxin B beads. Following dialysis against endotoxin-free PBS, the recombinant CD14 was filtered, aliquoted and stored at (−)20° C. The amount of endotoxin remaining after dialysis was found to be negligible (less than 10 ng/ml).

In some experiments, naturally occuring human soluble CD14 (nsCD14) was used. nsCD14 was purified from the urine of patients with nephrotic syndrome by affinity chromatography as previously described. Bazil V. and J. L. Strominger *J. Immunol.*, 147: 1567 (1991).

D. Recombinant soluble CD14 binds LPS in the presence of LBP.

To determine whether the recombinant soluble CD14 protein produced by insect cells is functionally active, studies were performed to assess whether it is able to interact with LPS-LBP complexes in the absence of other membrane proteins.

To assess the ability of rsCD14 in solution to compete with immobilized rsCD14 for LPS, four-fold serial dilutions of natural or recombinant sCD14 (64 μg/ml) or mouse IgG2a (64 μg/ml) were made in PBS containing 0.1% gelatin and added to bLPS at a final concentration of 1 μg/ml in the presence of purified rabbit LBP at a final concentration of 0.35 μg/ml; the mixture was then incubated for 30 min at 37° C. before transfer of 0.1 ml to each well of a plate which had been coated with rsCD14 at a concentration of 16 μg/ml as described above. To assess the ability of LPS to compete with bLPS for binding to immobilized rsCD14, 4-fold serial dilutions of LPS (64 μg/ml) in PBS/0.1% gelatin were added to the rsCD14 coated wells in the presence of purified rabbit LBP at a final concentration of 0.35 μg/ml; the plates were incubated 1 hour at 37° C. before the addition of bLPS at a final concentration of 4 μg/ml. The plates were then incubated 2 h at 37° C. and bound bLPS was measured as described.

The binding of biotinylated LPS (bLPS) to rsCD14 in the presence of purified rabbit LBP was measured by a solid-phase assay. To test the saturation binding properties of rsCD14 binding, wells of a MaxiSorp microtiter place (Nunc, Naperville, Ill.) were coated with 0.1 ml aliquots of natural (nsCD14) or recombinant soluble CD14 (rsCD14, 16 μg/ml) in 0.2 M acetate buffer, pH 5.0 or purified murine IgG2a (16 μg/ml) (Pharmingen, San Diego, Calif.) in 0.05M carbonate buffer. After an overnight incubation at 4° C., the wells were emptied and incubated with 0.15 ml of 0.5% gelatin (Sigma, St. Louis, Mo.) (prepared in the relevant coating buffer) for 30 min at 37° C. to reduce non-specific binding. After incubation, the wells were washed three times with 0.3 ml PBS containing 0.1% gelatin. LPS (*E. coli*, 0111:B4, Sigma) was biotinylated as previously described (A. Haziot et al., *J. Immunol.*, 151: 1500 (1993)) and two-fold serial dilutions of bLPS made in PBS containing 0.1% gelatin were added (0.1 ml) to each well.

To determine the extent of binding of bLPS in the presence of LBP, purified rabbit LBP (Haziot et al., *J. Immunol.* 150: 5556 (1993); Ishii et al., *Circul. Res.* 73: 15 (1993)) was added to bLPS at a final concentration of 40 $\mu$g/ml. The plates were incubated for 4 h at 37° C. in 100% humidity and then washed four times with PBS containing 0.1% gelatin. Bound bLPS was detected using streptavidin-alkaline phosphatase (GIBCO/BRL) (0.1 ml/well), diluted in PBS-gelatin (0.1%) to a streptavidin concentration of 20 ng/ml. After a 30 min incubation at RT, the wells were washed four times as described above and p-nitrophenyl phosphate (2 mg/ml in freshly prepared substrate buffer [10% diethanolamine, 0.5 mM $MgCl_2$, pH 9.8]) was added to the wells. The absorbance at 405 nm was read after 30 or 60 min on a THERMOmax microplate reader (Molecular Devices Corp., Menlo Park, Calif.). The absorbance obtained for wells coated with gelatin alone was subtracted from the absorbance obtained for each sample.

Figure 1B:
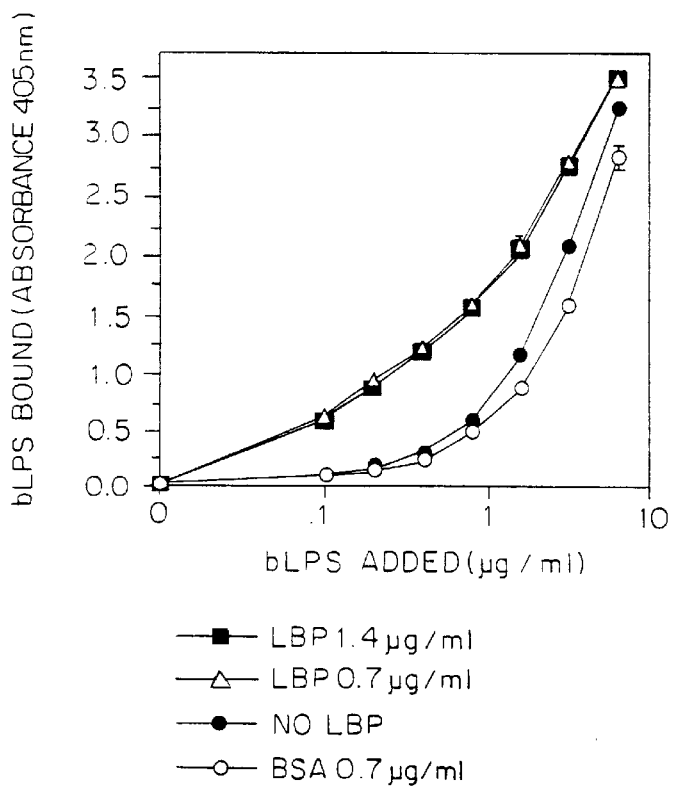

As shown in FIG. 1A, in the presence of LBP (40 $\mu$g/ml), bLPS binds strongly to immobilized rsCD14 and this binding is saturable. The results of binding assays performed at different concentrations of LBP showed that the maximal binding of bLPS to rsCD14 was similar in the presence of 20 and 40 $\mu$g/ml LBP (data not shown), indicating that LBP was not a limiting factor in this reaction. When immobilized lgG was substituted for the rsCD14, a small amount of non-specific binding was observed.

To compare the binding of natural and recombinant sCD14 to LPS-LBP, the binding bLPS-LBP to immobilized natural nsCD14 was also measured. The results shown in FIGS. 1A–1B indicate that nsCD14 binds slightly less bLPS-LBP than rsCD14; half maximal binding was reached with 3.2 and 5.6 $\mu$g/ml for rsCD14 and nsCD14, respectively. This difference may reflect partial denaturation of natural CD14 which might have occurred during the purification procedure. To investigate the effect of LBP on the binding of LPS to rsCD14, binding assays were performed in the presence or absence of LBP. As shown in FIG. 2B, bLPS binds rsCD14 in the absence of LBP. However, in the presence of low concentrations of LPS (0.1 and 0.2 ng/ml), the addition of LBP (0.7 $\mu$g/ml) strongly enhanced this binding, with a 6 to 7 fold increase in bound bLPS. Increasing the concentration of LBP TO 1.4 $\mu$g/ml did not further enhance the binding of bLPS to rsCD14. Interestingly, the enhancing effect of LBP is progressively abrogated when the concentration of bLPS increases. When bLPS is used at 6.4 $\mu$g/ml, LBP does not enhance the binding of bLPS to rsCD14.

Figure 2:
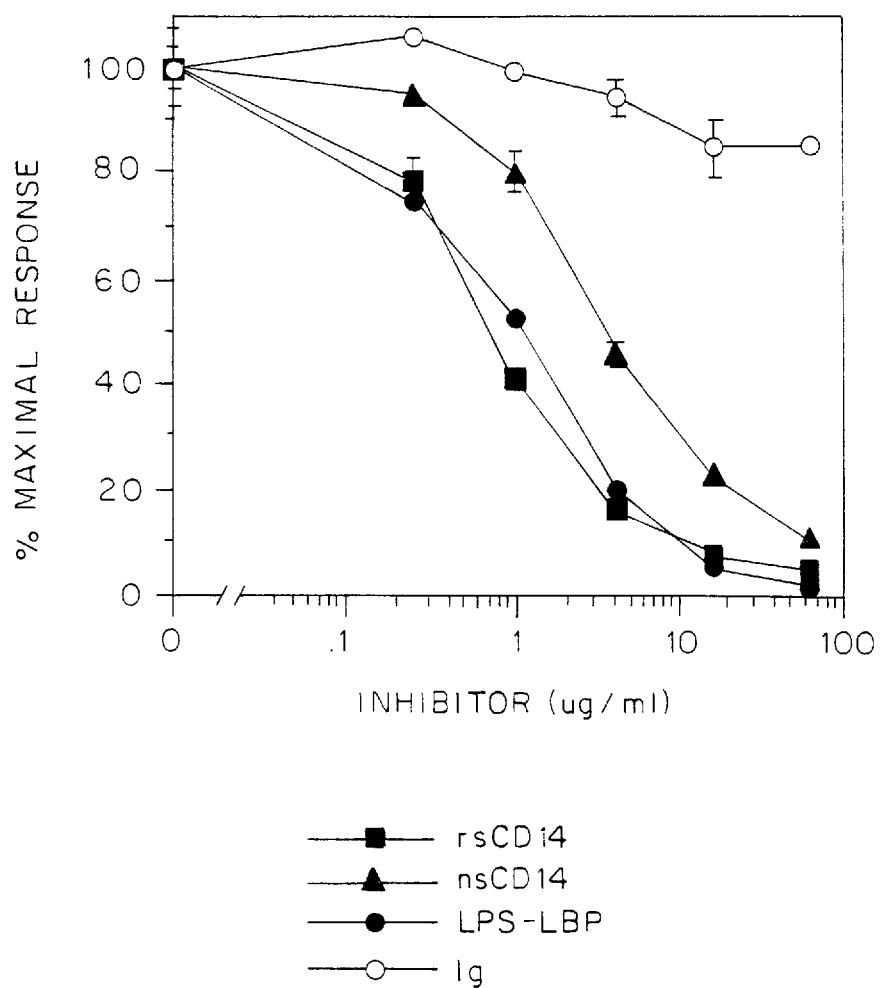
FIG. 2 depicts the inhibition of bLPS binding to immobilized rsCD14 in the presence of LBP by increasing amounts of unbound rsCD14, unbound nsCD14, unlabeled LPSLBP, or unbound murine IgG. Plates were coated with rsCD14 at 64 μg/ml. Increasing concentrations of rsCD14, nsCD14, or murine IgG were preincubated with purified bLPS (1 μg/ml) and LBP (350 ng/ml) and added to the wells. Specific binding was calculated by substraction of the amount of bLPS bound to wells coated with PBS-gelatin (0.5 %). Closed square, unbound rsCD14; closed triangle, unbound nsCD14; closed circle, unlabeled LPS (and LBP); open circle, unbound murine IgG. The results are representative of two assays.

To further demonstrate the specificity of the rsCD14-LPS interaction, the binding of bLPS-LBP to immobilized rsCD14 was analyzed in the presence of increasing concentrations of free rsCD14, free nsCD14 or unlabelled LPS complexed to LBP. Plates coated with rsCD14 at 16 $\mu$g/ml were tested for the binding of bLPS (1 $\mu$g/ml) in the presence of LBP (350 ng/ml) and increasing amounts of rsCD14, nsCD14 or LPS complexed to LBP (350 ng/ml) or murine lgG (used as a control). As shown in FIG. 2, rsCD14 and nsCD14 as well as LPS-LBP, strongly inhibit the binding of bLPS-LBP to immobilized rsCD14 while Ig has no effect.

E. Soluble CD14 inhibits the LPS-induced activation of monocytes and neutrophils in vitro in a dose-dependent fashion.

The effect of rsCD14 and of a monoclonal antibody to human CD14 on the LPS-induced activation of immune system cells was assessed by incubating monocytes or neutrophils in the presence of different concentrations of complexes ("LPS:LBP") composed of lipopolysaccharide ("LPS") and serum LPS-binding protein ("LBP"), in the absence or presence of either rsCD14 or of the monoclonal antibody.

The LPS was obtained from commercial sources (Sigma). LBP was purified from rabbit acute phase serum according to Tobias et al. *J. Exp. Med.* 164:777 (1986). LPS:LBP complexes were formed in sterile polypropylene tubes (Falcon #2063) by incubating varying amounts of sonicated LPS (obtained from wild type *Salmonella minnesota* and diluted in RPMI-Hepes [GIBCO/BRL, Gaithersburg, Md.]) with 60 ng purified rabbit LBP at 37° C. for 30 min. The total volume of the reaction was 100 $\mu$l.

Monocytes or neutrophils were added to the pre-formed complexes in the presence or absence of either the monoclonal antibody (MoS39) to human CD14 or of soluble CD14, in a final volume of 400 $\mu$l of RPMI-Hepes, and incubated for 3 hours at 37° C. in 5% $CO_2$. Following incubation, viability was 98–100% as determined by trypan blue exclusion.

Activation of the immune system cells was measured by collecting the cell-free supernatants and assaying for TNF activity, using either an ELISA assay (UBI, Lake Success, N.Y.) or a more sensitive MTT cytotoxicity assay. T. Mosmann, *J. Immunol. Methods* 65:55 (1983). The latter assay was performed using WEHI-2F cells (provided by Dr. E. Lattime, Thomas Jefferson Medical School, Philadelphia, Pa.), which are a TNF-sensitive clone of WEHI-164 cells. Briefly, 50 $\mu$l of serially diluted cell-free culture supernatants obtained from stimulated neutrophils were added to individual wells in 96 well plates. WEHI-2F cells ($2\times10^3/50$ $\mu$l of RPMI-HEPES containing 50% FBS) were added to each well. In order to distinguish the cytotoxicity due to TNF$\alpha$ from other cytotoxic activities, the assay was performed simultaneously in the presence of a neutralizing anti-TNF$\alpha$ monoclonal antibody (UBI, Lake Placid, N.Y.) at 1 $\mu$g/ml. Following a 36-hour incubation at 40° C. [as described by D. R. Branch et al., *J. Immunol. Methods.* 143:251 (1991)] in 5% $CO_2$, 25 $\mu$l of a solution of 3-[4,5-dimethylthiazol-2-yl]-2,5-diphenyltetrazoliumbromide (MTT [5 mg/ml, Aldrich, Milwaukee, Wis.]) prepared in PBS was added and the samples were further incubated for 5 hours at 40° C. Isopropanol containing 0.04N HCl and 2.5% DMSO (0.15 ml) was added to each well and the resulting formazan crystals were dissolved by vigorous pipetting. The optical density at a wavelength of 570 nm was determined using a Coulter (Hialeah, Fla.) microplate reader. TNF units were calculated by Probit analysis. R. S. Wallis, *J. Immunol. Methods* 145:267 (1991). Maximum cytotoxicity was measured using human recombinant TNF$\alpha$ units detected by this assay was 1 unit/ml.

Figure 3A:
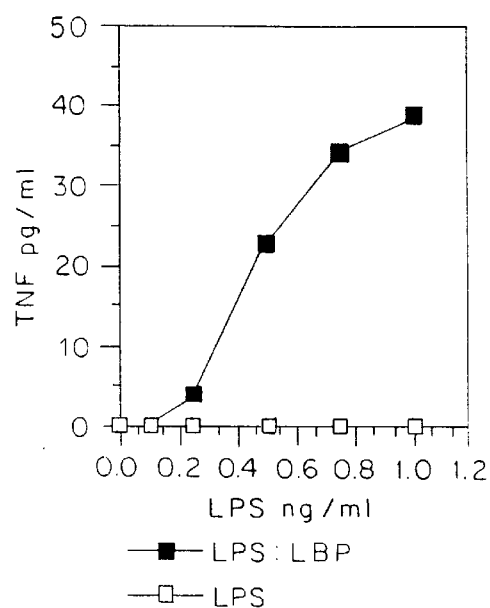
FIGS. 3A–3D demonstrate that either a monoclonal antibody to human CD14 (MoS34) or recombinant soluble CD14 itself can inhibit the LPS-induced activation of murine monocytes or neutrophils.
Figure 3B:
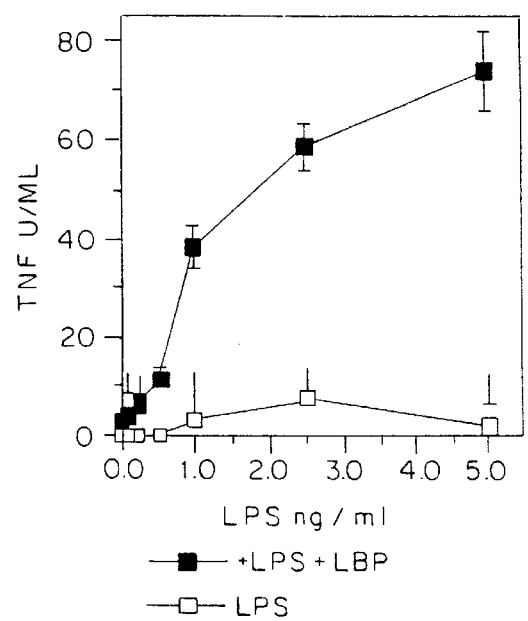

FIGS. 3A and 3B show that the LPS:LBP complex stimulates monocytes (FIG. 3A) and neutrophils (FIG. 3B) to release tumor necrosis factor ("TNF") in a dose-dependent fashion.

In FIG. 3A, PBMC ($1\times10^6$) consisting of $1.7\times10^5$ monocytes (as assessed by morphological examination of Wright-Giemsa stained samples) were added to LPS:LBP complexes or to LPS alone and incubated for 3 hours at 37° in 5% $CO_2$. Cell-free supernatants were assayed for the presence of TNF by the ELISA assay mentioned above.

In FIG. 4B, neutrophils ($3.4\times10^6$) were added to LPS:LBP complexes or to LPS alone and incubated for 3 h at 37° C., 5% $CO_2$. Since the levels of TNF released by the neutrophils were not detectable by the above ELISA assay, cell-free supernatants were assayed for TNF activity as described above in a cytolytic assay using WEHI-2F cells. No cytotoxicity was detected when WEHI-2F cells were treated with a neutralizing anti-TNF antibody, indicating that all cytotoxicity observed was due to TNF. Data are mean values ±SD of duplicate samples and are representative of four independent experiments.

Figure 3C:
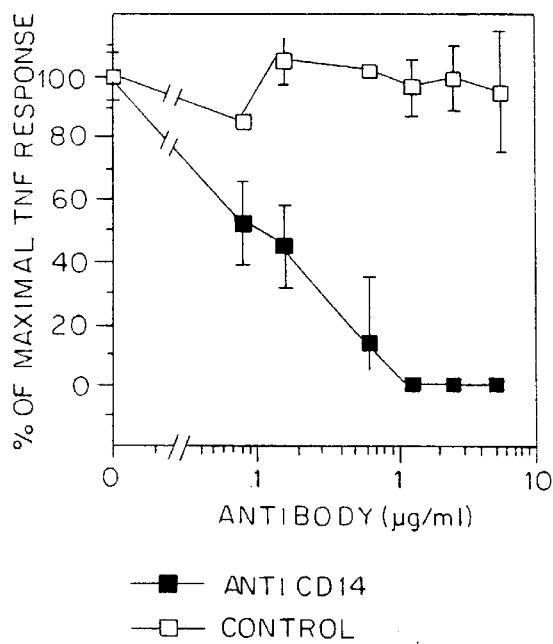

The monoclonal antibody to CD14 inhibited the secretion of TNF by neutrophils stimulated with LPS:LBP complexes (FIG. 3C). Neutrophils ($3.5 \times 10^6$) were incubated for 30 min at 4° C. in the presence of dilutions of F(ab')$_2$ fragments (stock=0.63 mg/ml) of an anti-CD14 monoclonal antibody or dilutions of F(ab')$_2$ fragments (stock=0.69 mg/ml) of an isotype-matched irrelevant antibody. LPS:LBP complexes were formed as described above with a final LPS concentration of 5 ng/ml. Antibody-treated cells were added to the LPS:LBP complexes at a final concentration of and incubated for 3 hours at 37° C. The cell-free supernatant was then assayed for TNF activity using WEHI-2F cells. Data shown are mean values of duplicates and are representative of three independent experiments. When error bars are not seen, they fall within the symbol. The results of this experiment suggest that anti-CD14 antibodies administered in vivo might reduce or inhibit the response to LPS.

Figure 3D:
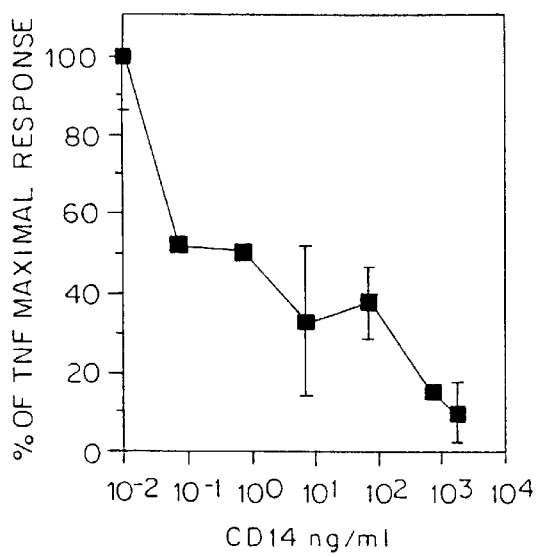

FIG. 3D demonstrates that soluble CD14 will inhibit LPS:LBP-induced monocyte activation (measured by secretion of TNF). For this experiment, monocyte preparations similar to those described in FIG. 4a were treated with recombinant CD14 and were assayed for the production of TNF by the ELISA assay. Results represent duplicates. When error bars are not seen, they fall within the symbol. This result suggests that soluble CD14 administered in vivo might reduce or inhibit the response to LPS.

E. rsCD14 can protect mice in vivo from LPS-induced death

The ability of rsCD14 to protect animals in vivo from the effects of endotoxin-induced septic shock was tested by injecting mice with LPS in the presence and absence of rsCD14.

Example 2. Intraperitoneal Co-Injection of LPS and CD14

Five or six week-old male C57B1/6J mice, weighing approximately 20 g each, were injected intraperitoneally with freshly sonicated *Salmonella minnesota* LPS (dosage: 10 μg LPS per gram mouse body weight, supplemented with 68 μg of rsCD14, in a final volume of 0.4 mls PBS). Control mice were injected with 10 μg LPS per gram mouse body weight in 0.4 mls PBS in the absence of rsCD14. Control and experimental mice were then were observed for a period of seven days.

TABLE 1

| LPS | rsCD14 | % SURVIVAL |
|---|---|---|
| 10 μg/g body weight | 0 | 20% (1/5) |
| 10 μg/g body weight | 68 μg | 100% (3/3) |

As shown in Table 1, 100% of the mice that were injected simultaneously with LPS and rsCD14 survived, as compared to only 20% of the mice that were injected with LPS alone. These results demonstrate that rsCD14 can interact with LPS to neutralize its inducement of symptoms and effects of sepsis, and that rsCD14 can inhibit the in vivo response to LPS including death due to endotoxin shock.

Example 3. Separate Intraperitoneal Injections of LPS and CD14.

Figure 4:
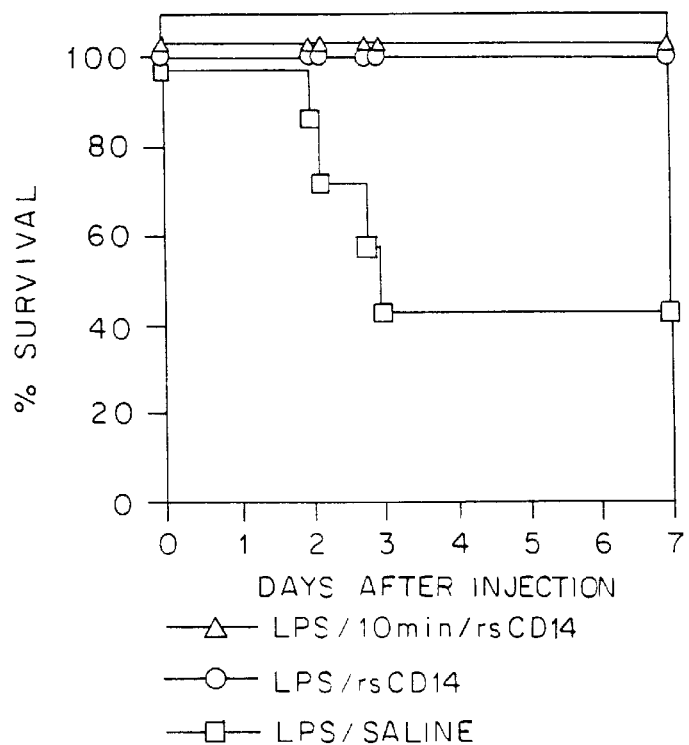
FIG. 4 illustrates the protection provided by intraperitoneally injected rsCD14 against intraperitoneally injected endotoxin-induced lethality. Eight week old mice were weighed and injected i.p. with an $LD_{50}$ of LPS (*Salmonella Minnesota*, wild type, 12 μg/gbw) in 0.1 ml saline followed by a second i.p. injection given immediately of either rsCD14 (12 μg/gbw, open circle) or saline (open square) . In some cases the second injection of rsCD14 (12 μg/gbw) was given after a 10 minute delay [open triangle]. Each group consisted of 7 mice. p=0.0175 by the two-tailed Fisher exact test.

In a separate experiment, C57BL/6J mice were injected intraperitoneally (i.p.) with an $LD_{50}$ of wild type LPS (*Salmonella Minnesota*) followed by an i.p. injection of human rsCD14 either immediately or after a 10 minute delay. At 12 μg/gbw (gram body weight) the mice in both experimentally treated groups exhibited symptoms of sensitivity to LPS, such as prostration, ruffled fur, diarrhea and eye exudate. However, human rsCD14 given immediately after the LPS challenge or 10 minutes later significantly reduces death in mice (p<0.02) (FIG. 4).

Example 4. Separate Intraperitoneal Injection of LPS and Intravenous Injection of rsCD14

Figure 5:
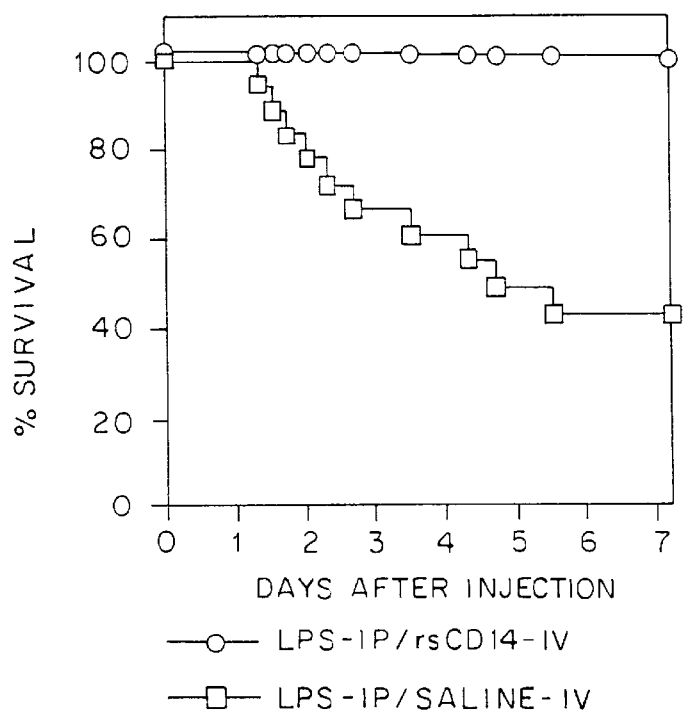
FIG. 5 illustrates the protection provided by intravenously injected rsCD14 against intraperitoneally injected endotoxin-induced lethality. Eight to nine week old C57BL/ 6J mice were weighed and injected i.p. with an $LD_{50}$ of LPS (*Salmonella Minnesota*, wild type, 13 μg/gbw) in 0.2 ml immediately followed by an intravenous (i.v.) injection of 12 μg/gbw rsCD14 (open circle, n=10) or saline (open square, n=18) in 0.2 ml. p=0.0039 by the two-tailed Fisher exact test.

To exclude the possibility that the protective effect of rsCD14 was due to neutralization of the LPS by rsCD14 in the peritoneal cavity, LPS and rsCD14 were administered by different routes. Mice were injected intraperitoneally with an $LD_{50}$ of LPS followed immediately by an intravenous injection of human rsCD14 (12 μg/gbw) or saline. As shown in FIG. 5, rsCD14-treated mice were significantly protected (p<0.005) and the level of protection was similar to that achieved with the intraperitoneal injection in FIG. 4.

Example 5. In Vivo Effect of rsCD14 on Blood TNFα Levels.

To analyze the events occurring in rsCD14-treated animals, mice were injected with LPS, followed by rsCD14 or saline as described above, and bled at different timepoints (30, 80, 135 minutes following LPS administration). TNFα levels in the serum were then measured by a bioassay, as described in A. Haziot, B. Tsuberi, S. M. Goyert, *J. Immunol.* 150, 5556 (1993).

As shown in FIG. 6, at 80 min mice injected with 30 μg/gbw of rsCD14 had slightly lower levels of TNFα in their serum than control mice while at 135 min they had significantly lower levels (p<0.001). Mice injected with 50 μg/gbw rsCD14 secreted significantly lower amounts of TNF than control mice at both 80 (p<0.0001) and 135 min (p<0.0001). These results suggest that the effects of rsCD14 in mitigating LPS-induced death are directly due to its ability to inhibit the production of TNFα by LPS-activated cells.

F. rsCD14 can inhibit TNFα secretion in human cells:

In order to determine whether the results with mice were extensible to human subjects, the effects of rsCD14 on human cells were studied.

Peripheral blood from healthy adult volunteers was drawn using heparin as an anticoagulant. Stock solutions of rsCD14 or globulin-free BSA (Sigma) (1 mg/ml) were prepared in PBS and depleted of endotoxin by combining each reagent with washed polymyxin B-coated beads (Sigma) at a ratio of 4:1 (v/v), followed by rotation for 30 min at RT and filtration of the supernatants through 0.45 micron Millex filters (Millipore, Bedford, Mass.). LPS (*Salmonella minnesota* wild type, [List Biological Laboratories, Campbell, Calif.]). The sample was then resuspended at 5 mg/ml in non-pyrogenic water (Baxter, Deerfield, Ill.), sonicated, aliquoted and stored at −80° C. Dilutions of LPS were made in non-pyrogenic water immediately before use.

PBMC were isolated as described (A. Haziot et al., *J. Immunol.* 141: 547–552 (1988)) and resuspended at $2.7 \times 10^6$/ml in activation medium (RPMI [GIBCO/BRL] containing 10 mM HEPES (GIBCO/BRL) and 1% autologous plasma). LPS was diluted to 0.5μg/ml and added to aliquots of the activation medium (0.1 ml); after a 10 min incubation at 37° C., activation medium (0.1 ml) containing various concentrations of rsCD14 was added to the LPS solution and the mixture was incubated for 30 min at 37° C. Aliquots of 0.3 ml of a suspension of PBMC ($8 \times 10^5$ cells) were then added; the final volume was 0.5 ml and the final concentration of LPS was 0.5 ng/ml. Following a 3 h incubation at 37° C., the TNFα concentration in the cell-free supernatant was determined by ELISA using anti-TNFα mAb 199 and 195 as the capture and detection antibodies, respectively (Boehringer Mannheim Corp., Indianapolis, Ind.). Using recombinant human TNFα (UBI, Lake Placid, N.Y.) as a standard, the detection limit of the assay was found to be 10 pg/ml.

Macrophage cell lines were established as described (23) by passage of non-adherent macrophages spontaneously released from macrophage cultures. Briefly, PBMC were isolated (A. Haziot et al., *J. Immunol.* 141: 547–552 (1988)), the concentration of the monocytes was determined by morphological analysis of cells stained with Wright's stain (Sigma) and the cells were cultured ($0.5 \times 10^6$ monocytes/ml) in DMEM (GIBCO/BRL) supplemented with 5% autologous plasma, 10 mM HEPES, and 0.25% heparin (1000 U/ml, ESI Inc., Cherry Hill, N.J.) at 37° C. and 5% $CO_2$. The culture medium was changed every 3 days. After 3 changes, the non-adherent cells were 90% α-Naphtyl esterase positive and 100% CD14 positive and secreted TNFα in the presence of purified rabbit LBP (7) and LPS at concentrations as low as 0.1 ng/ml (data not shown). Assays done in the presence of rsCD14 were done as follows: LPS was diluted to 50 ng/ml and added to 0.1 ml RPMI-10 mM HEPES containing purified rabbit LBP to reach final concentrations of 0.25 ngLPS/ml and 100 ngLBP/ml in the final volume of reaction (0.5 ml); the mixture was incubated 30 min at 37° C. and 0.1 ml of RPMI-10 mM HEPES containing various concentrations of rsCD14 was added; after a 30 min incubation at 37° C., 0.3 ml of a suspension of macrophages ($8 \times 10^4$ cells) was added and the samples were incubated for 3 h at 37° C. and 5% $CO_2$. The TNFα concentration in the cell-free supernatant was determined by bioassay using WEHI-2F cells and the MTT cytotoxic assay (24) as previously described (7). TNFα units were calculated by Probit analysis. (25).

Heparinized whole blood (0.25 ml) was dispensed in 1.5 ml polypropylene tubes and varying amounts of rsCD14 or globulin-free BSA prepared in 50 μl RPMI (GIBCO/BRL) was added and the tubes were gently shaken. LPS at a concentration of 50 ng/ml was added to the samples to yield a final concentration of 0.1 or 0.25 ng/ml. After gentle shaking of the tubes, the mixtures were incubated for 3 h at 37° C. After a 2 min centrifugation at 16000×g, the supernatants were collected and assayed for TNFα by ELISA as described above.

Figure 7A:
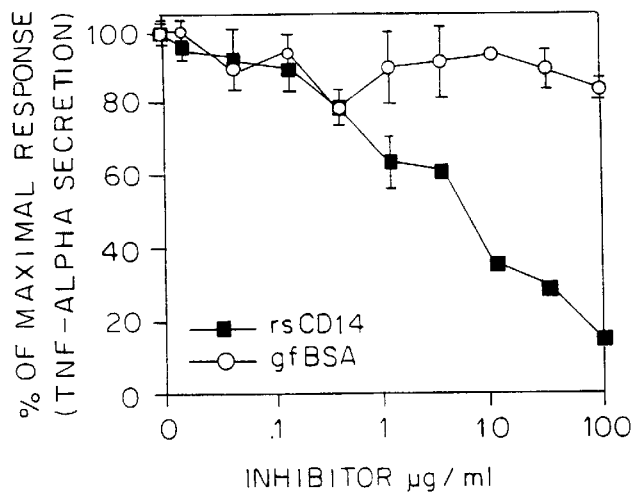
FIGS. 7a–7c. Inhibition of LPS-induced TNF-α production.
Figure 7B:
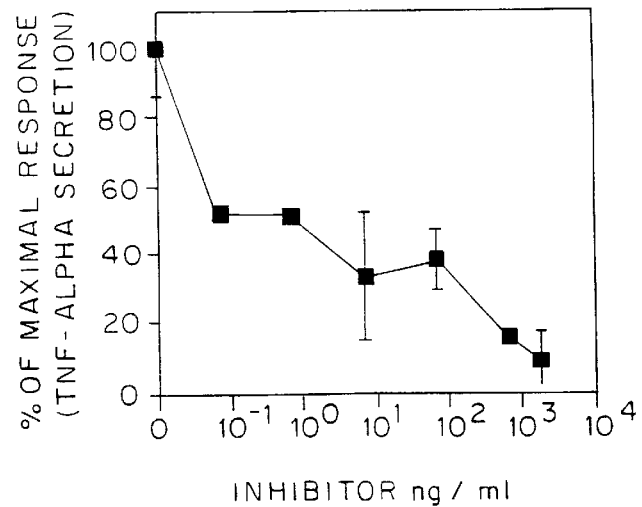
Figure 7C:
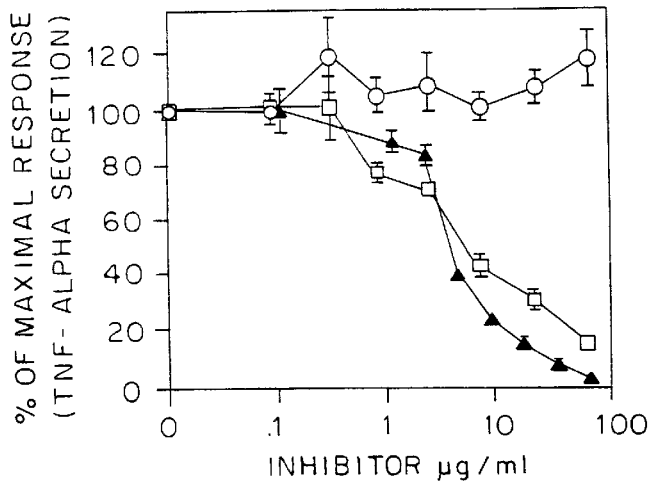

Since, as shown above, rsCD14 can bind complexes of LPS and LBP, studies were performed to determine whether rsCD14 is able to block the secretion of TNFα induced by LPS using three different cell populations—PBMC, cultured macrophages and cells in whole blood (FIGS. 7A–7C). For these experiments low concentrations of LPS were used which specifically affect the CD14-dependent pathway of LPS-induced cell activation. PBMC were incubated in 1% autologous plasma in the presence of LPS (0.5 ng/ml) and increasing concentrations of rsCD14 and, following incubation, TNFα was measured in the cell-free supernatant. Results in FIG. 7A show that rsCD14 strongly inhibits the secretion of TNFα induced by LPS. Similarly, the TNFα secretion of cultured macrophages incubated with LPS at 0.25 ng/ml and purified LBP at 0.1 μg/ml is strongly inhibited by rsCD14 (FIG. 7B).

Since the activation of cells in whole blood approximates the conditions which exist in vivo (Desch, C. E. et. al, *Lymphokine Res.* 8: 141 (1989)), an analysis was perfomed of the effects of rsCD14 on the LPS-induced secretion of TNFα in the presence of a concentration of LPS which is physiologically relevant (0.1 ng/ml [29]) and at a concentration 2.5 times higher (0.25 ng/ml). FIG. 7C. The addition of rsCD14 to whole blood immediately before adding LPS results in the inhibition of secretion of TNFα. At the concentration of 0.25 ng LPS/ml, 50% of the TNFα secretion is reached with a concentration of 7.2 μg/ml of added rsCD14 and when rsCD14 is added to a final concentration of 67 μg/ml 84% of the TNFα secretion is inhibited. It should be noted, however, that the concentration of endogenous rsCD14 has been reported to be approximately 4 μg/ml. Thus, if it is assumed that endogenous soluble CD14 has a similar affinity for LPS, the apparent ID50 of 8 μg/ml; at this concentration of LPS, 96% of the TNFα secretion is inhibited with the addition of 71 μg rsCD14/ml (final concentration).

Since soluble CD14 has been shown to modulate the responses to LPS of human cells, it thus appears that the results with mice are fully extensible to human system.

F. Fragment of soluble fragment of CD14.

Additional studies were performed to identify whether fragments of the CD14 molecule may be useful in treating symptoms associated with sepsis. A peptide having the following amino acid sequence, comprising amino acids 143 to 168 of the rsCD14 sequence, was ordered from Peninsula Labs:

A E L Q Q W L K P G L K V L S I A Q A H S L N F S C (SEQ ID NO:1)

To test whether the peptide retained the properties of the parent molecule, a competitive binding assay was used. A. Haziot et al.,*J. Immunol.*, 151: 1500 (1993). Briefly, rsCD14 (100 μl/well, 16 μg/ml) was added to ELISA plates. The wells were blocked with 0.5% gelatin diluted in PBS. Serial dilutions of the 26 mer peptide were made in PBS containing 0.1% gelatin and added to biotinylated LPS (final concentration, 1 μg/ml). Purified rabbit LBP was also added (final concentration, 1 μg/ml). The samples were incubated for 30 min at 37° C. and were then added to the rscd14-coated wells and the plates were incubated 4 h at 37° C. Bound LPS was detected using a streptavidin-alkaline phosphatase detection system as previously described.

Figure 8:
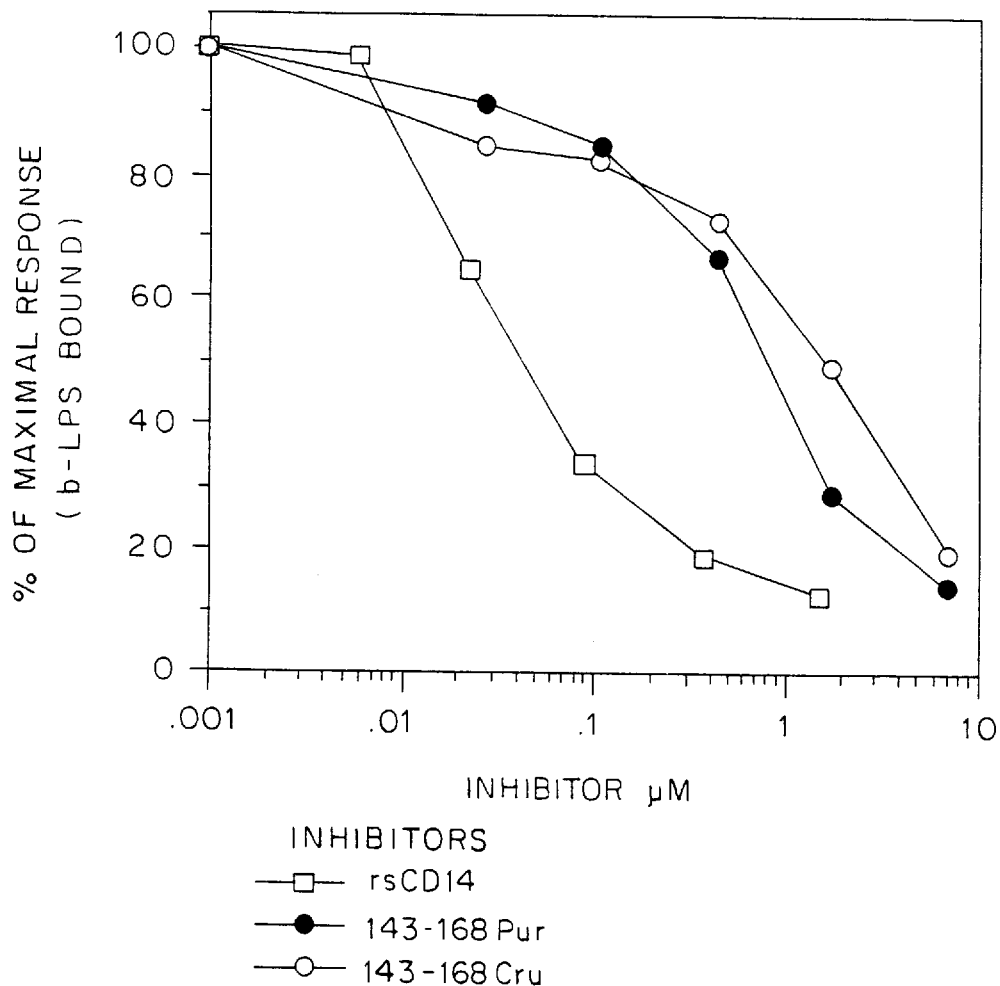
FIG. 8 illustrates that the CD14 fragment claimed herein can bind to LPS.

The data is shown in FIG. 8 for the purified peptide (pur) and for the crude peptide (cru). The data is plotted as % maximal response. The rsCD14 appears to inhibit more efficiently at lower concentrations, however, at the higher concentration (1.7 μM), purified peptide inhibits almost as well (72%) as rscd14 (84%). When the peptide is used at a concentration of 7 μM, the amount of inhibition (84%) is the same as that achieved with 1.7 μM rscd14.

G. Analysis

These studies demonstrate that rsCD14 protects animals injected with LPS from death, and strongly suggest that a principal mechanism is competition with the CD14 receptor. This finding is surprising in view of the demonstrated agonist effects of soluble CD14 on the endothelial response to LPS; as mentioned above it has been proposed that the activation of endothelial cells plays a role equal to or greater than the role of monocyte activation in the induction of endotoxic shock. A. Haziot, G. W. Rong, V. Brazil, J. Silver, S. M. Goyert, *J. Immunol.* 151: 1500 (1993); U. Grunwald et al., *J. Immunol. Methods* 155: 225 (1992).

Although the normal level of sCD14 in mouse serum is not known, it may be similar to that of humans (2 to 4 μg/ml). U. Grunwald et al., *J. Immunol. Methods* 155: 225 (1992). Thus, the amount of rsCD14 that was injected in mice for the studies described above may represent a 25-fold increase over native sCD14.

It has recently been proposed that the activation of endothelial cells plays a role equal to or greater than the role of monocyte activation in the induction of endotoxic shock. U. Grunwald et al., *J. Immunol. Methods* 155: 225 (1992). One possible explanation is that in vivo, endothelial cells do not respond to LPS and rsCD14 in the same manner as they do in vitro, or that the endothelial response represents only a small component of the total cellular response to LPS.

Alternatively, although LPS and rsCD14 may activate endothelial cells, a concomitant strong activation of monocytes/macrophage may be necessary to induce endothelial damage as recently suggested (J. Pugin, R. J. Ulevitch, P. S. Tobias, *J. Exp. Med.* 178: 2193 (1993)); since rsCD14 blocks the monocyte/macrophage activation of LPS (A. Haziot, G. W. Rong, V. Bazil, J. Silver, S. M. Goyert, *J. Immunol.* in press), endothelial cell activation would then remain limited.

Modifications and variations of the methods for producing preparations of soluble CD14 (for example, the use of different expression systems, such as bacterial expression systems, for expressing recombinant CD14; or the use of different plasmids and viruses than the ones that were used in the examples mentioned below; or the use of nucleic acids that encode proteins that are essentially homologous to the CD14 used herein; or the use of a different isolation and purification scheme that yields a purified product that possesses essentially the same properties of the soluble CD14 described herein) and of the methods for using soluble forms of CD14 to prevent, ameliorate or treat the symptoms of sepsis (such as using a different way of administering the sCD14), will be obvious to those skilled in the art from the foregoing detailed description of the invention. Such modifications and variations are intended to come within the scope of the appended claims.

3. A method according to claim 1 wherein said soluble mammalian CD14 fragment CD14 is administered by injection.

4. A method according to claim 1 wherein said soluble mammalian CD14 fragment is administered by intraperitoneal injection.

5. A method according to claim 1 wherein said soluble mammalian CD14 fragment is administered at the time said mammal is exposed to an agent that induces a symptom associated with sepsis that is mediated by the CD14 receptor.

6. A method according to claim 1 wherein said soluble mammalian CD14 fragment is administered at a time that is selected from the group of times that consists of: before said mammal exhibits at least one symptom associated with sepsis and while said mammal exhibits at least one symptom associated with sepsis.

7. The method of claim 1 wherein said symptom associated with sepsis is caused by a Gram-negative bacterium.

8. The method of claim 1 wherein said symptom associated with sepsis arises upon exposure to an LPS.

9. The method of claim 1, wherein the condition is sepsis.

10. The method of claim 1, wherein the administration is of a soluble fragment of human CD14.

I claim:

1. A method for preventing or treating a condition that is mediated by the action of lipopolysaccharide (LPS) or membrane-bound CD 14, comprising administering a soluble mammalian CD14 fragment which has LPS binding activity in an amount effective to prevent or treat at least one symptom of a condition that is mediated by the action of said LPS or membrane-bound CD14.

2. A method according to claim 1 where said condition is selected from the group consisting of sepsis, gram negative bacteremia, autoimmune disease, and tissue rejection.

11. The method of claim 1, wherein the administration is of a peptide which is a soluble fragment of human CD14, but whose pattern of glycosylation is different from that of naturally occuring CD14.

12. A fragment according to claim 1, wherein said fragment comprises the following amino acid sequence SEQ ID NO:1:

A E L Q Q W L K P G L K V L S I A Q A H S L N F S C.

* * * * *